United States Patent
Johnson

(10) Patent No.: US 10,382,039 B2
(45) Date of Patent: Aug. 13, 2019

(54) MICROSENSOR DETECTION PROCESS

(71) Applicant: Mark B Johnson, Potomac, MD (US)

(72) Inventor: Mark B Johnson, Potomac, MD (US)

( * ) Notice: Subject to any disclaimer, the term of this patent is extended or adjusted under 35 U.S.C. 154(b) by 0 days.

(21) Appl. No.: 16/196,654

(22) Filed: Nov. 20, 2018

(65) Prior Publication Data

US 2019/0158092 A1 May 23, 2019

Related U.S. Application Data

(60) Provisional application No. 62/588,583, filed on Nov. 20, 2017.

(51) Int. Cl.
*H03K 19/0175* (2006.01)
*H04B 1/40* (2015.01)
*H04B 5/00* (2006.01)

(52) U.S. Cl.
CPC ....... *H03K 19/017581* (2013.01); *H04B 1/40* (2013.01); *H04B 5/0062* (2013.01)

(58) Field of Classification Search
CPC . H03K 19/017581; H04B 5/0062; H04B 1/40

USPC .......................................................... 326/38
See application file for complete search history.

(56) References Cited

U.S. PATENT DOCUMENTS

| | | | |
|---|---|---|---|
| 7,047,792 B1* | 5/2006 | Bhethanabotla | G01N 29/022 73/24.01 |
| 9,329,154 B1* | 5/2016 | Allendorf | G01N 29/022 |
| 9,726,646 B1* | 8/2017 | Brocato | G01N 29/2437 |
| 9,835,585 B2* | 12/2017 | Fife | G01N 27/4145 |
| 2006/0066824 A1* | 3/2006 | Knappe | G03F 7/70916 355/30 |
| 2010/0223999 A1* | 9/2010 | Onoe | H03H 3/08 73/579 |
| 2010/0236322 A1* | 9/2010 | Kogai | G01N 29/022 73/53.01 |

\* cited by examiner

*Primary Examiner* — Don P Le
(74) *Attorney, Agent, or Firm* — J. Nicholas Gross, Esq.

(57) ABSTRACT

A process is disclosed for using microsensors elements embedded in or on articles for detecting target chemical and/or target environmental conditions of interest, including materials hazardous to human health and/or associated with illegal activity. The microsensor elements can be fabricated on a single semiconductor chip, and can be made indetectable to facilitate secure surveillance of potentially illegal activities.

15 Claims, 7 Drawing Sheets

FIG. 5        500

710 → Application:
Aerosol is sprayed on the inside surfaces of a rental car trunk 715 → Distribution:
Car is rented to a surveillance target.

720 → Sampling:
Hazardous material stored in trunk will be detected by RIMs.

700

725 → Recovery:
Rental car is returned.

730 → Readout:
Optical source and detector test RIMs coating inside surfaces of trunk.

FIG. 7

MICROSENSOR DETECTION PROCESS

RELATED APPLICATION DATA

The present application claims the benefit under 35 U.S.C. 119(e) of the priority date of Provisional Application Ser. No. 62/588,583 filed Nov. 20, 2017, which is hereby incorporated by reference. This application is also related to the following applications, all of which are filed on this same date and incorporated by reference herein:

Microsensor Chemical Detection System & Elements; Ser. No. 16/196,596
Microsensor Chemical Detection Mixture; Ser. No. 16,196,629
Microsensor Coated Article; Ser. No. 16/196,640

STATEMENT AS TO GOVERNMENT RIGHTS

The present application is related to an application Ser. No. 14/133,055 that was filed during a time when the inventor was employed by the Naval Research Laboratory as part of Task Area MA02-01-46, Work Unit T042-97, and was developed as a result of efforts associated with NRF grants funded by MEST (2010-0000506, 2011-0012386 and 2012-0005631), the industrial strategic technology development program funded by MKE (KI002182), the Dream project, MEST (2012K001280), GRL and the Office of Naval Research. To the extent they are not otherwise alienated, disclaimed or waived, the government may have certain limited rights to use, practice or otherwise exploit some or all portions of the inventions herein.

FIELD OF THE INVENTION

The present application is directed to processes that use miniaturized, customized sensors incorporated on the surface or within the body of the article for the purpose of detecting a target element, compound or environmental condition. The miniaturized sensors are applied, among other ways, using an aerosol delivery system, a paint/printing process, or as part of a manufacturing process for the article. The invention is particularly suited for detecting hazardous materials in security applications, including for scanning mail, packages, etc.

BACKGROUND

Common hazardous materials, including explosives, corrosives and biohazards, are typically solid or liquid. Associated with these materials are volatile (gaseous) chemicals. These volatiles may be the gaseous form of the hazardous material or may be a molecule that derives from a simple chemical reaction of the hazardous material with ambient conditions.

The traditional method of detecting chemical or biological agents, including those associated with hazardous materials, is described with the schematic sketch in FIG. 1. The sketch and discussion of the sketch are summarized from material in Ref. [1]. A conventional sensor system 100 that studies or identifies the chemical components of an analyte (sample) 110 consists of: (1) a chemical detection or recognition element 120, (2) a transducing element 130, and (3) a signal-processing element (including memory) 140. The chemical detection element 120 is composed of some sensing material. It interacts with a sample on a substrate or in the environment and generates a response. The transducer 130 reads the response from the chemical detection element and converts it into a quantifiable signal in a format that can be used as data that are input to the signal processor. The signal processor 140 analyzes the input and determines if a target substance has been detected. It may also quantify the relative amount of the substance. The Readout 150 from the system processor includes an output 160 that is provided to a larger information system or network.

The chemical detection element 120 is the basis of the system. It is characterized by its response, recovery, selectivity and sensitivity. Categories of materials for the chemical detection element include metal and metal oxide semiconductors, solid electrolytes, insulators, catalytic materials, polymers and composites. The detection element may be unique and customized for a given target molecule. The detection element may undergo a structural change or may respond to electric, electrochemical or optical stimulation, and the transducer 130 functions by sensing a change of state associated with one of these responses. The detection element may respond by exhibiting a plurality of different states, either discrete or an analog spectrum of states. The signal processor 140 interprets the information from the transducer to confirm that a change has occurred in the detecting element and identifies the changed state, or identifies which of a plurality of states is present. In such instances the entire system/process of identifying and confirming the presence of the target material is performed by elements distinct from the article (in this case the analyte or substrate) itself. An example of this prior art approach is a stationary (static) system that detects biohazards. In a specific example, the target is anthrax and the article in question (a postal letter or package) is processed by a customized, isolated chamber as the article passes through a mail delivery facility.

System 100 may have multiple and changeable components, but typically is a macroscopic system with a large physical footprint. The signal processor 140 may be a central computing system or a smaller system such as a desktop or laptop computer. The chemical detection element 120 and a matched transducer 130 may be designed for detection of a specific target substance and a variety of these components may be connected to the signal processor.

In the example given above, an article (postal letter or package) serves as a substrate that may or may not include the target analyte and the article is provided to the apparatus in the course of commerce and transactional traffic. In another method of operation, samples are gathered from the field, brought to the system and introduced to the system for analysis. The system apparatus has a large footprint and is relatively expensive. Although the system may have changeable components, the flexibility is severely limited. These are disadvantages of this prior art.

Recent developments in microfabrication have enabled the invention of new kinds of chemical or biological sensor systems. The new system is chip-based, miniaturized, adaptable to different targets and inexpensive. The system builds on the older concept of a system-on-a-chip. A system-on-a-chip may include one or more sensors, digital information processing circuits, memory, and means for input and output of data. The Remote Independent Microsystem (RIM) was disclosed in U.S. Pat. No. 9,432,021. A RIM is micro- or nano-fabricated with dimensions smaller than a traditional system-on-a-chip. It is inexpensive and designed to be expendable after a single use. It operates with very low power and has a long operational lifetime. Detection of chemical or biological agents was mentioned in '021 but this application deserves further consideration.

The new sensor system requires chemical detection elements 120 that are fabricated on micro- or nano-processed chips. The detection elements can be tailored to respond to a specific agent or to a class of agents. Several detection elements with uniquely tailored responses can be fabricated on a single chip. A selection of one element (or of a subset of several element) can be made programmatically by activating the appropriate areas of the chip.

A variety of chemical detection elements are suitable for microfabrication on chips. As one example, there have been many developments in the last two decades concerning the use of carbon nanotubes (CNTs) as detecting elements, typically in the form of a dedicated/integrated sensing/detection portable system. An interaction between a target molecule and a CNT changes the electric resistivity of the CNT. The interaction occurs when the volatile molecule comes in contact with a surface of the CNT. This change of resistive state is the basis of the CNT sensor.

It is not currently practical to fabricate a robust sensor using a single CNT. Therefore an array of CNTs is typically fabricated on top of a pair of interdigitated thin film metal electrodes to form a detecting element. The transducer is a circuit that measures the resistance of the array. The transducer may have the simple form of a current source and voltage detector or the inverse, a voltage source and current detector. The resistance measurement of the transducer is sent to the signal processor where the value is compared with an initial reference resistance value stored in memory. A comparison of the values determines whether an interaction has occurred and the presence of the target molecule can be deduced/confirmed.

An example of a detecting element 200 using CNTs is shown in FIG. 2. Thin film metal wires 220 and 240 form a pair of interdigitated current and voltage electrodes. An array of CNTs 230 is distributed across the surface of the leads and they adhere to the surface. To measure the average resistance of the array, a small current is applied from 220 to 240 and a voltage is measured from 220 to 240. Alternatively, voltage can be applied and current measured. Detector arrays of this kind have been fabricated with lateral dimensions on the order of 10 microns [2].

The process using CNTs is flexible enough that it can be modified in a number of ways in order to detect a variety of target molecules using other forms of chemical interactions. For example, the CNTs can be coated with a thin layer of a chemically active material such as a polymer. An interaction occurs when the volatile molecule comes in contact with the polymer. If the polymer is altered or destroyed by the interaction, the resulting change in the surface state of the CNT causes a corresponding change in resistance. The resistance is measured by the transducer and the process for deducing the presence of the target proceeds in the same way as described above. A different choice of chemical coating results in sensitivity to a different target molecule.

Chemical detection elements based CNTs represent an approach that has successfully demonstrated microfabricated prototypes with dimensions on the order of ten microns or less. Other techniques also are plausible. Traditional detection elements (fabricated with macroscopic dimensions) commonly use polymers. Polymers are organic macromolecules dominantly comprised of carbon and hydrogen atoms, and include heteroatoms such as nitrogen, oxygen, sulfer, phosphorous and etc. as minor constituents. They are characterized by high tailorability, having a broad range of properties and versatility. Both the bulk and surface of a polymer may contain active functional groups which can respond as a chemical sensor. Properties that can be sensed by a transducer include physical and/or chemical (such as mass or volume), electrical (resistivity) and optical.

In addition to these chemical targeted sensors, other environmental condition detecting elements in printed electronic form are known in the art and are sufficiently small (~4 cm by 8 cm) to be affixed (with an adhesive or similar technique) to packaging or other articles of interest. These elements are sensitive to conditions such as temperature, humidity, pressure, flow or light. As a specific example, in transporting certain pharmaceutical products care must be taken to ensure that they are not exposed to temperatures over a certain threshold. See e.g., U.S. Pat. No. 9,742,466 incorporated by reference herein.

Some additional useful background information for the present invention can be found in: Fundamentals of Sensing Materials. Volume 3: Polymers and Other Materials, edited by Ghenadii Korot Tcenkov, Momentum Press, LLC, New York, N.Y. (2010); Chapter 1, Polymers in Chemical Sensors, B. Adhikari and P. Kar, page 2 and FIG. 1.1; and Li, J., Lu, Y., Ye, Q., Cinke, M., Han, J., and Meyyappan, M., Nano Lett., Vol. 3, p 929 (2003); Li, J. *Carbon Nanotubes: Science and Applications*, Chapter 9, Editor: M. Meyyappan, CRC Press, Boca Raton, Fla., USA (2004) both of which are incorporated by reference.

SUMMARY OF THE INVENTION

An object of the present invention, therefore, is to overcome the aforementioned limitations of the prior art. It will be understood from the Detailed Description that the inventions can be implemented in a multitude of different embodiments. Furthermore, it will be readily appreciated by skilled artisans that such different embodiments will likely include only one or more of the aforementioned objects of the present inventions. Thus, the absence of one or more of such characteristics in any particular embodiment should not be construed as limiting the scope of the present inventions.

An object of the present invention, therefore, is to overcome the aforementioned limitations of the prior art. It will be understood from the Detailed Description that the inventions can be implemented in a multitude of different embodiments. Furthermore, it will be readily appreciated by skilled artisans that such different embodiments will likely include only one or more of the aforementioned objects of the present inventions. Thus, the absence of one or more of such characteristics in any particular embodiment should not be construed as limiting the scope of the present inventions.

An object of the present disclosure therefore is to overcome some of the limitations of existing chemical detection systems, specifically, by making the detection elements smaller so that they can be deployed into new environments, are easier to deploy and are more functional.

A related object therefore is to provide a chemical detection system tha can be situated on a single semiconductor chip, comprising: a sensor circuit configured with a resistance state that is responsive to the presence of a target chemical and/or target environmental condition when exposed to a target environment; a transducer coupled to the sensor circuit configured to detect the resistance state and generate an output corresponding thereto; and a magnetoelectronic (ME) processing circuit coupled to the transducer and including one or more magnetoelectronic gates adapted to perform a first sequence of operations during an operational mode on the output from the transducer; a detection output is generated by the ME processing circuit having a detection value based on the first sequence of operations confirming the presence of the target chemical and/or target environmental condition; the ME processing circuit is configured to not consume power in a quiescent mode; a non-volatile memory coupled to the ME processing circuit for storing the detection value; a readout substance situated in a storage chamber of the single semiconductor chip; and one or more micromechanical structures responsive to the detection output, and adapted to cause the first readout substance to be released from the storage chamber in response to the detection value; with this type of structure a presence of the target chemical and/or target environmental condition can be determined by detecting the first readout substance released from the chamber.

In preferred embodiments the sensor made of a carbon nanotube (CNT). The CNT sensor circuit can also be coated with a polymer that reacts in the presence of the target chemical.

A second storage chamber can be connected to the storage chamber for storing a second readout substance. In some applications, a membrane separating the storage chamber and the second storage chamber is provided, and which is adapted to be ruptured by the one or more micromechanical structures to permit mixing of the first readout substance and the second readout substance. For some applications, a third readout substance can be caused to result from the mixing. In other applications the membrane rupture permits release of the first readout substance to an exposed external portion of the single semiconductor chip.

The target chemical can be a chemical and/or biological agent hazardous to living organisms.

Depending on the application, the chemical detection system and the first readout substance can be made to be detectable or substantially undetectable to an unaided human visual system.

Because of their small size, one or more single semiconductor chips can be affixed to or embedded in a paper based substrate or an article of clothing. They can also be incorporated and made part of a solid powder or liquid mix.

Due to their low expense and ease of manufacturability, they can also be implemented as one-time disposable detectors of the target chemical. They can be deployed in significant quantities in a large distributed targeted area to increase the likelihood of detecting target environmental conditions and/or chemicals.

The system can also include a transmitter and antenna situated on the single semiconductor chip adapted for communicating a result of the detection output using electromagnetic radiation. For example, the antenna can be adapted for near field communications with a separate target chemical interrogation system, which can be microwaves, pulses, etc. The antenna enables passive readout and is activated by a readout pulse generated by the ME circuit. A voltage bit stream from the stored detection value can be superposed with a reflected microwave signal to form a signal transmitted to an interrogating receiver.

In other applications, the first chemical readout can be detected using an optical reader responsive to a wavelength of light reflected by the first readout substance and/or a separate chemical resulting from the first readout substance.

A further aspect of the invention concerns a detection mixture of chemical detection elements, comprising: a first component including one or more non-detecting chemical elements in the detection mixture; the chemical detection elements being incorporated as a second component of the detection mixture and comprising a single integrated circuit on which is situated: a sensor element configured with a sensor state responsive to the presence of a target chemical when exposed to a target environment; a transducer coupled to the sensor element and configured to detect the sensor state and generate an output corresponding thereto; and a magnetoelectronic (ME) processing element coupled to the transducer and adapted to perform a first sequence of operations during an operational mode on the output from the transducer; wherein a detection output is generated by the ME processing element having a detection value based on the first sequence of operations confirming the presence of the target chemical; a readout substance situated in a storage chamber of the single semiconductor chip; and one or more micromechanical structures responsive to the detection output, and adapted to cause the first readout substance to be released from the chamber in response to the detection value; with this mixture, a presence of the target chemical can be determined by detecting the first readout substance released from the chamber.

Depending on the target environment or use, the first component of the detection mixture can be a solid powder, including for example dry toner particles contained within a printer cartridge. The chemical detection elements are engineered and manufactured to be approximately the same size as toner particles constituting the first component of the detection mixture. In other applications the first component of the detection mixture is a liquid ink or dye, which be applied and adhere to an article such as a fabric, a paper based substrate, and similar materials which can be coated with a surface layer. In still other environments the mixture can be incoporated as part of regular liquid suspension, or an aerosol suspension within a pressurized container, adapted with a nozzle to spray the detection mixture onto a target surface. The detection elements can be configured to respond to environmental conditions, including temperature, humidity, light or radiation associated with the target environment. In such instance, one or more thin film metal resistance elements can be used to respond to a target environmental. These environmental condition detection elements can be incorporated within an RFID tag and made readable by a passive dipole antenna microwave based reader.

Yet another object of the present invention is to provide a physical article adapted with chemical detection capability based on integrated chemical detection elements, comprising: a first body portion of the article; the chemical detection elements being incorporated on a surface of the first body portion; and each of the chemical detection elements comprising a single integrated circuit on which is situated: a sensor element configured with a sensor state responsive to the presence of a target chemical when exposed to a target environment; a transducer coupled to the sensor element and configured to detect the sensor state and generate an output corresponding thereto; a magnetoelectronic (ME) processing element coupled to the transducer and adapted to perform a first sequence of operations during an operational mode on the output from the transducer; a detection output can be generated by the ME processing element having a detection value based on the first sequence of operations confirming the presence of the target chemical; a readout substance situated in a storage chamber of the single semiconductor chip; one or more micromechanical structures responsive to the detection output, and adapted to cause the first readout substance to be released from the chamber in response to the detection value; a presence of the target chemical having made contact with or in the vicinity of the article can be determined by detecting the first readout substance released from the chamber.

Depending on the application, the physical article can be an article of clothing, paper, packaging, and similar articles that could come into contact with a target chemical and to which the elements can be affixed or embedded. In some security applications the elements are incorporated within an ink mixture on a sheet of paper, or as part of the fibers making up the body of the paper itself.

Other related objects of the invention pertain to methods of detecting hazardous materials, in which the chemical detection elements are embedded or affixed to including the process of: providing a first physical article; embedding a chemical detection element onto a surface portion of the physical article, wherein each of the chemical detection elements comprises a single integrated circuit (IC); generating a sensor state based on a sensor element on the single IC, which sensor state responds to the presence of a target chemical on and/or near the first physical article; generating a transducer output with a transducer on the single IC coupled to the sensor element which detects the sensor state and generates an output corresponding thereto; interpreting the transducer output with a magnetoelectronic (ME) processing element on the single IC; the ME processing element generating a detection value based on the interpreting the output confirming the presence of the target chemical; and generating a chemical payload output responsive to the detection output on the single IC to indicate prior exposure of the first physical article to the target chemical, either directly on or in some cases in the vicinity thereof.

Again, depending on the target application, the chemical detection element is applied as a liquid, as a spray, or in solid form to the physical article. In surveillance situations, the article can be placed in a target environment and recovered after a predetermined period where it can be read out. In some surveillance instances the physical article can be part of an enclosure for a room, a transportation vehicle, a fixture or piece of furniture within a room, etc.

In other instances the surveillance article is in a paper form (letter, flyer, package, coupons, etc.) that is expected to be handled by a human target for monitoring and detection of minute traces of the target chemical on such person's hands, clothes, body, etc.

DESCRIPTION OF THE DRAWINGS

FIG. 7 is a simplified flowchart of the basic steps of a preferred chemical sensor detection process using RIMs dispersed as an aerosol implemented in accordance with the teachings of the present disclosure.

DETAILED DESCRIPTION OF THE INVENTION

The present disclosure provides new embodiments of micron-sized magnetic based chemical/environmental condition detectors that are well suited for a number of new applications, and which are affixed or applied directly as a thin coating or layer to articles using printed, coated or sprayed processes, including through aerosol applicators. These detectors are based on variants of magnetoelectronic devices previously disclosed by the present inventor.

For example, my U.S. Pat. No. 9,432,021 (incorporated by reference herein) disclosed a novel low power micro- or nano-processor called a Remote Independent Microsystem (RIM). The RIM family includes system-on-a-chip devices based on magnetoelectronic gates, which are versatile and be configured as both memory and/or logic circuits. These devices are extremely inexpensive, disposable, and optimal for single-use cases. In one category of these devices, the RIM includes one or more sensors (detection elements), a transducer circuit that tests the value of the sensors, a signal processing logic circuit that interprets the result of the test, a nonvolatile memory that stores results of the tests, a timing or input circuit that determines when (and how often) tests are performed, and a readout circuit that displays the result of the test in a form that can be read by an external operation. The RIM is introduced in column 5 line 6 of '021 and a detailed description begins on column 9 line 58. An embodiment of a RIM is illustrated with a sketch in FIG. 3B of '021. Other forms of CMOS based hybrid semiconductor devices which can function as both logic and memory may be suitable for applications of the present invention as well. For example, in U.S. Pat. No. 8,988,103 to Liu (incorporated by reference herein) a floating gate based CMOS device is described that employs capacitive coupling for both logic and memory functions, to implement a particular type of boolean logic circuit: a majority circuit. Other similar devices with hybrid functionality may be employed in some embodiments of the present detectors to effectuate the necessary processing and memory functions described herein.

Figure 1:
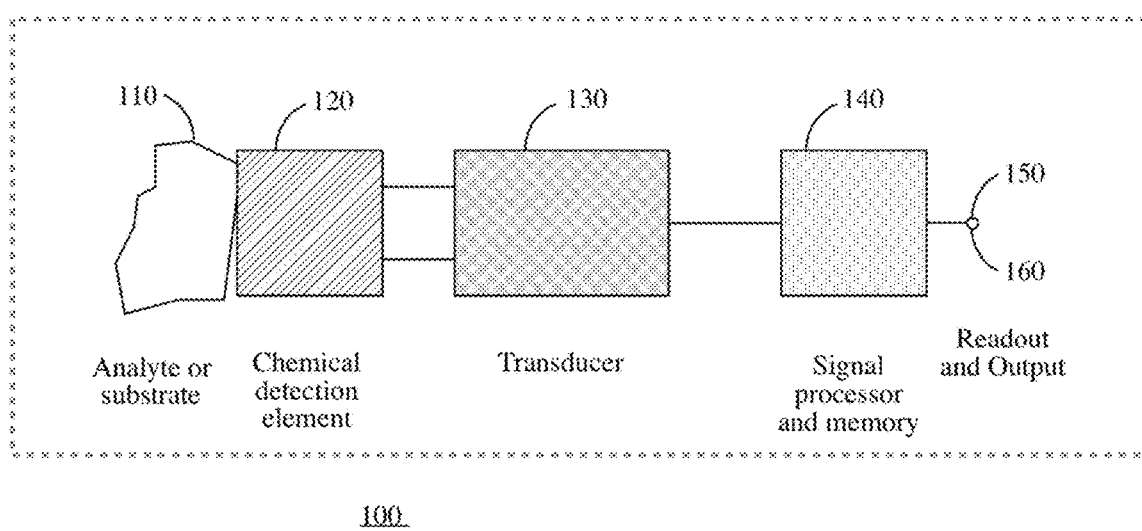
FIG. 1 is a simplified diagram of the basic components of a conventional chemical sensor system.
Figure 2:
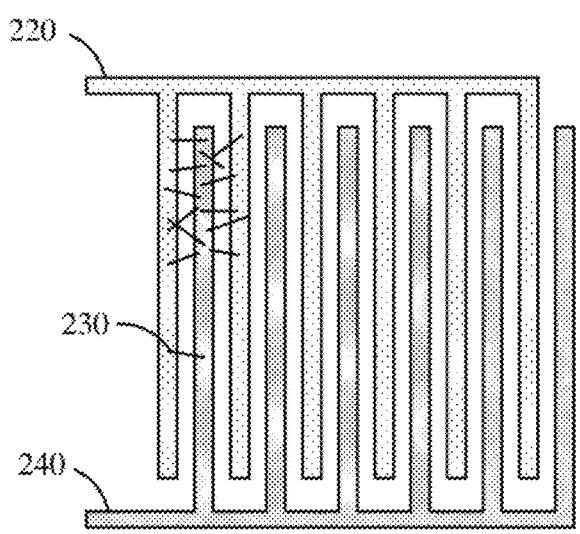
FIG. 2 is a top view sketch of a carbon nanotube (CNT) based detector.
Figure 3:
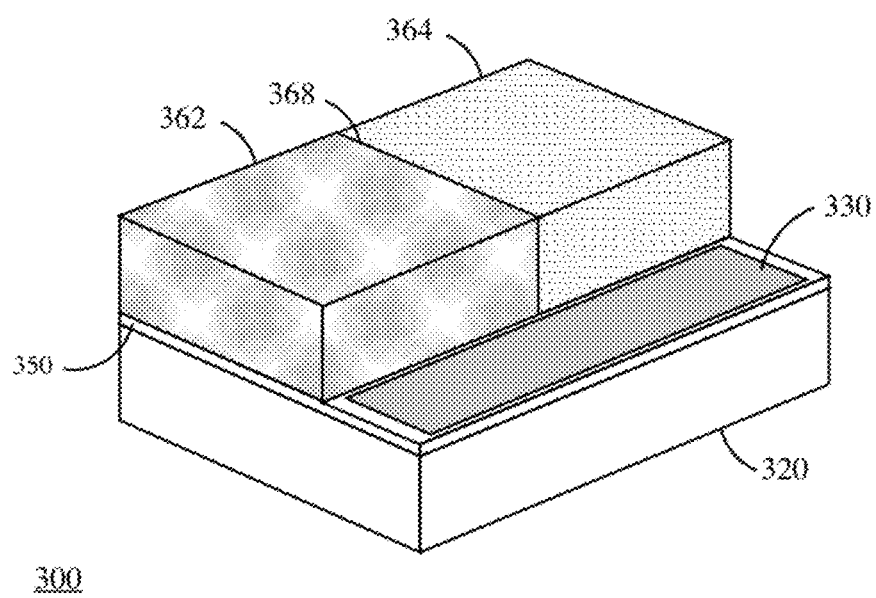
FIG. 3 shows the structure of a RIM based chemical sensor system implemented in embodiments of the present invention.

A similar embodiment is shown in FIG. 3 herein. As in FIG. 3B of '021, FIG. 3 illustrates a perspective sketch of a preferred embodiment of a typical package for an integrated system on a chip RIM 300. The figure shows a number of the components discussed above, including:

Signal processor logic and memory components for the RIM system situated on a common substrate 350;

battery 320;

CNT based sensor [e.g. FIG. 2] 330;

Components for one form of passive readout 362, 364 and 368.

Details of active and passive readout functions are discussed below. In this preferred embodiment, one part of the passive readout is a fluid chemical 1 that is retained in a hollow storage volume or chamber 362 (this was also referred to as a "payload" in '021). A second part of the passive readout is fluid chemical 2 that is retained in a separate hollow storage volume or chamber 364. A thin membrane 368 preferably separates chemicals 1 and 2. Chemicals 1 and 2 are chosen to be reactants in a chemical process in which the product of the process is a dye molecule (not shown). In this preferred embodiment, the dye molecule results if the membrane is ruptured so that chemicals in the two payloads are permitted to interact or mix. A rupture in membrane 368 can be caused to occur when the sensor exceeds a target threshold and the circuit 350 activates a microelectronic mechanical structure (MEMS) of any well-known suitable forms in the art near the membrane (not shown). It will be understood that membrane 368 may include one or more separate layers or materials, and that the boundary surfaces of chambers 362 and 364 are preferably transparent. This embodiment was discussed in '021 in the context of applications where the RIM could be employed in an aqueous environment and chambers 362 and 364 protected chemicals 1 and 2 from the environment.

Variations of this technique will be apparent to those skilled in the art from the present teachings. For example, Chemical 1 can be a dye molecule that is initially stored in opaque chamber 362. Transparent chamber 364 is initially empty. Activation of a MEMS structure ruptures membrane 368 and the dye molecule fills a portion of transparent chamber 364, where it can be detected by optical methods, including a human eye.

For applications discussed in this disclosure, RIMs 300 are typically deployed in a dry environment. For such cases another variation is simpler. A dye molecule is initially stored in opaque chamber 362 and chamber 364 is omitted. Activation of a MEMS structure ruptures membrane 368 and the dye molecule coats a substantial portion of the outside surface of the RIM package. The dye can be detected by optical methods and the presence of the dye does not hinder functions of the RIM.

Figure 4:
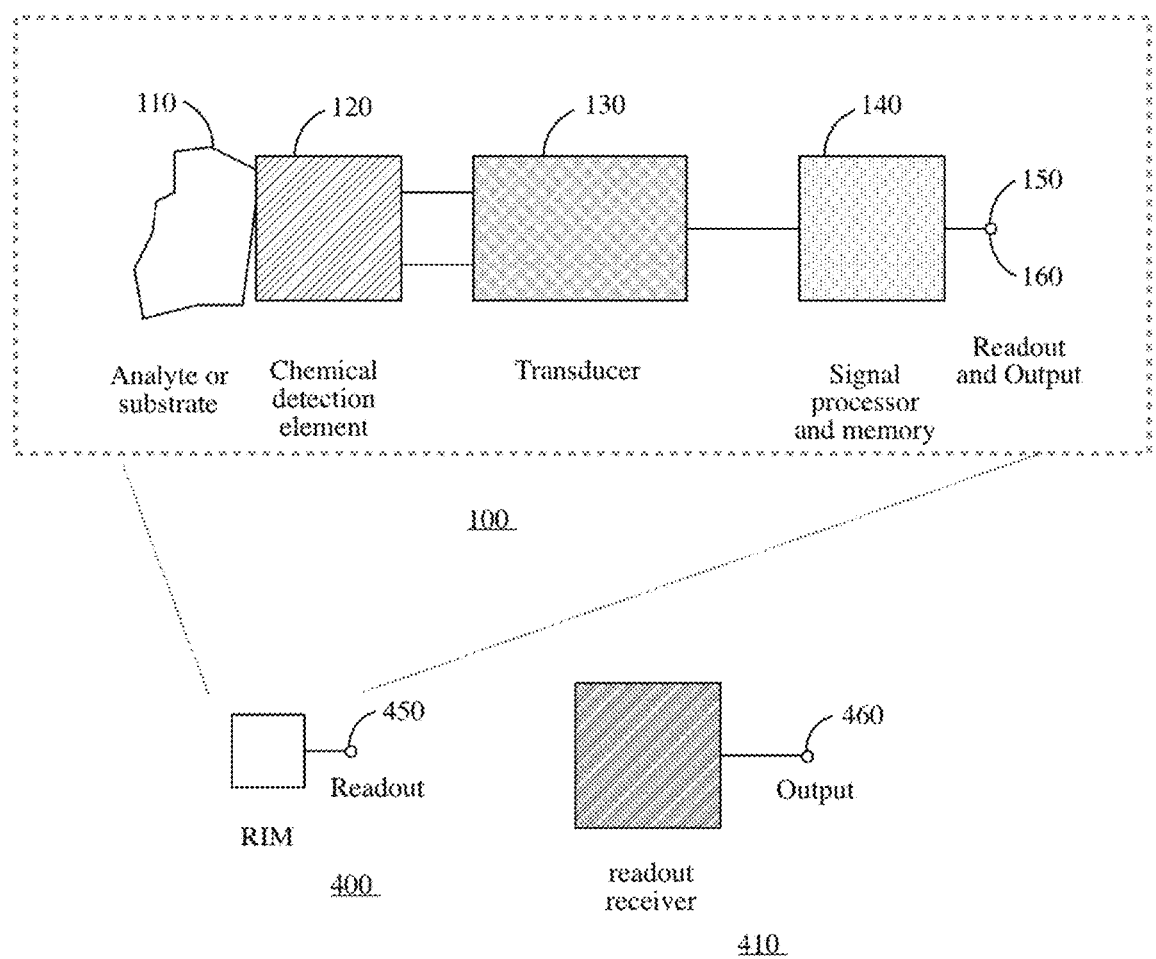
FIG. 4 is a simplified diagram identifying the basic components of a chemical sensor system implemented in accordance with the teachings of the present disclosure.

The presence of the dye on the exterior of the RIM 300 can be used to represent the result of the chemical detection process, a single bit of information that indicates the presence or absence of the target. It can be called a "readout molecule," and can be "read" using a "readout receiver" and a process described below. The selection of particular readout (or payload) chemicals can be determined using routine skill based on application goals, system requirements and the environment the sensor is to be used in. For example, in instances where human observation is to be used to detect an output, the resulting dye (in sufficient quantities) should be detectable to a human eye. In other instances, because of cost, convenience or security, the resulting dye can be engineered to be detectable only by additional machine assistance or interrogation, such as in the case of a change in infrared or ultraviolet, radiation, etc. Other examples will be apparent to those skilled in the art and further details are included below. In some applications, as noted herein, the detection system and the resulting readout substance (which, in a preferred approach is also a chemical) may be substantially undetectable to a human visual system to avoid detection, such as in an surveillance application Combining microfabricated detector elements, such as the CNT element of FIG. 2, with system-on-a-chip structures such as the RIM results in a new method of detecting chemical or biological agents associated with hazardous materials. The basic method was introduced in '021 and is described herein with further detail. Referring to the schematic drawing of FIG. 4, all of the components of system 100 are microfabricated on a single chip 400. A significant operational difference between macroscopic system 100 and microscopic system 400 is that the former is readily connected to a broad information system or network. By contrast, the readout signal of 400 is relatively weak and it must be received by a macroscopic subsystem 410 and then amplified and/or converted to a different format in order to make the output 460 available to a broader information system.

In the following sections, structures, means and methods for providing readout to a receiver 410 are described first. Following this, techniques for employing the novel chemical or biological sensor system are discussed.

A RIM 300 can provide output of results stored in memory in several ways and basic techniques were introduced by the inventor in US Patent '021. In a first method, a RIM with a sufficiently large battery can use active readout to transmit data to a receiver. The RIM includes a transmitter and transmitting antenna. Transmission could use convenient frequencies in the microwave band. In a preferred technique, the RIM employs a near field antenna as a compact alternative to a dipole antenna. For the purpose of this specification, the term near field antenna will be used in contrast with the more typical dipole antenna. Electromagnetic radiation has coupled electric and magnetic fields that oscillate together. A dipole antenna generates an oscillating electric field and the magnetic field is created simultaneously. The dipole antenna typically has a length of a quarter of a wavelength of the generated electromagnetic radiation. A near field antenna generates an oscillating magnetic field and the electric field is created simultaneously. This kind of antenna typically has a coil geometry and the spatial dimensions are unrelated to the wavelength and can be much smaller than the wavelength.

Near field antennas have been developed for commercial radio frequency identification (RFID) applications. An example of such an antenna is used for subcutaneous implantation in pets or humans. Dimensions of such a cylindrical antenna are approximately 1 mm in diameter and 2 mm in length. The operating frequency is tuned for the commonly used RFID frequency of 13.56 MHz, and the effective radius of transmission is 5 to 10 cm. Lithographic processing may result in a near field antenna with dimensions that are smaller by a factor of ten or more. It is important to note that the near field antennas developed for RFID can be used for either transmission or reflection (also called backscattering). The former is typically called active readout. The latter is passive readout and is described further below.

A second kind of readout and detection of the RIM state is passive and requires very little power. A RIM using passive readout can operate with a small battery and the overall RIM dimensions can be reduced significantly. Two forms of passive readout can be described. The first category relates to the description in '021 and the extended discussion above. A circuit can trigger an integrated MEMS (Micro Electro Mechanical Structure) or NEMS (Nan Electro Mechanical Structure) device that releases a readout molecule which has a chosen optical response. For the applications in this disclosure, the readout molecule preferable remains fixed to the surface RIM so that it can be more easily detected. One example is a dye molecule that reflects a conveniently chosen wavelength of light. A second example is a fluorescent molecule that can be excited by a light source and then fluoresced with a spectrum that's readily detected. In this form, the released molecule can be considered a readout molecule as it represents a single bit of information. It will be understood that a RIM may have one or more readout molecules in one or more chambers to indicate detection of different target chemicals.

The second form of passive readout employs the same antenna described above but used in a passive mode. An antenna tuned to the frequency of an input wave will reflect a small portion of the input power when the circuit impedance attached to the antenna differs from the intrinsic impedance of the antenna. In the simplest form, an appropriate antenna can be configured to be enabled or disabled by sending a current pulse through either a fuse or anti-fuse. As a specific example of this, the antennal coil can be fabricated to include a conducting wire fuse that forms a short circuit across the two terminals (refer also to '021). As fabricated, the antenna is disabled. A current pulse applied to the fuse destroys the fuse and enables the antenna. A bit of information is thereby represented by an enabled or disabled antenna, and therefore the presence or absence of a reflected pulse of microwave power in response to an interrogation pulse. The antenna can be called a readout reflector. Any RIM may have one or more readout reflectors, each tuned to a different resonant wavelength. The advantage of this technique is that it is simple and requires no on-chip power.

Alternatively, the antenna can transmit a string of data using an RFID technique, a well known method briefly described as follows. In the presence of incident microwave radiation at the tuned frequency, a portion of the power received by the antenna is converted to current and directed to a subcircuit consisting of a rectifier and capacitor (not shown). The rectified current charges the capacitor and the charged capacitor provides dc current to the other circuits of the RIM. A portion of this current may be used to generate microwaves transmitted by the antenna. Alternatively, a portion of the current is converted to a voltage and applied to the memory. The resulting readout current is modulated as a function of time and superposed with a small microwave transmission that is created in the form of reflected power. Readout of the nonvolatile memory cells has the form of a low frequency digitally modulated current that also is applied to the antenna. The result is a transmission of resonant frequency microwaves with an amplitude that is modulated by a bit-stream that contains the information stored in RIM memory. The modulated microwaves are received and decoded by standard techniques. An advantage of this form of readout is that it requires no on-chip power. Another advantage is that it can transmit a stream of many bits. Therefore, this technique can be used for a RIM that may have multiple sensors or that may include on-chip data processing that results in a relatively large amount of data.

Referring again to FIG. 3, the preferred embodiment of the simplified RIM 300 functions as a disposable, one-time detector of a target hazardous chemical (or chemicals). A volatile molecule associated with the targeted chemical adsorbs to the surface of chemical detecting array 330. A circuit in logic processor 350 is programmed to test the status of the sensor at periodic intervals. When a target molecule is present, the sensor voltage exceeds a threshold value. An activation circuit (not shown, but which may take any number of well-known forms) in processor 350 sends a voltage pulse to a MEMS device adjacent to membrane 368 (not shown) and the membrane ruptures. Chemicals 1 and 2 are then free to mix together and a dye readout molecule forms in the volumes 362 and 364. If the RIM is recovered, the status of the sensor is determined by measuring the value of an amplitude or intensity of reflectance of light having a wavelength corresponding to the color of the dye. If the RIM remains in a remote location that cannot be directly accessed, the status of the sensor is interrogated and determined in the same way using a broad and higher power beam of light. The reflection from a collection of RIMs in a larger area (several square meters) can be measured with an appropriate detector remotely as well for physical and chemical surveillance purposes.

The operational goal of the new approach is to take advantage of the microscopic size and low cost of microfabricated sensing chips such as RIMs. Large number of chips can be distributed widely, and techniques that involve attaching RIMs to common articles are discussed below. Detection of hazardous biological or chemical agents is increased because such approach only requires success of only a small fraction of a large number (i.e. hundreds or thousands) of distributed chips. The presence of the chips will preferably be unknown to observers and is harmless to the environment. The transmission of Readout data from any RIM 400 (FIG. 4) to a readout receiver 410 has limited range. For the case of either active or passive microwave transmission, the range might be the order of meters in the former case and the order of 10 cm in the latter case. For passive readout using a readout molecule, optic techniques can be used with a range varying from the order of 1 cm to the order of 10 meters. Operation of the overall approach involves techniques of chip dispersal, recovery, and operation of the readout receiver.

Figure 5:
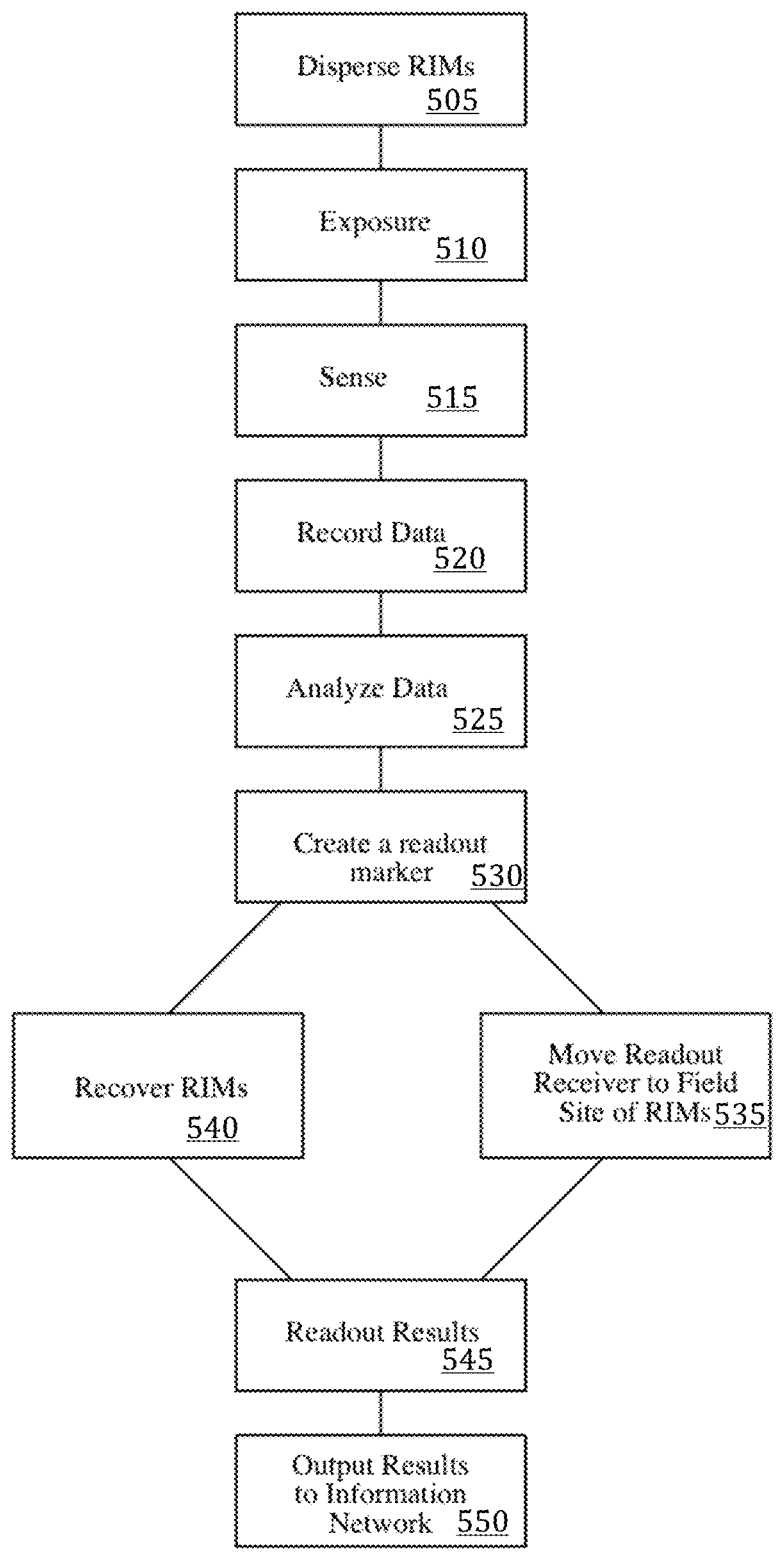
FIG. 5 is a simplified flowchart of the basic steps of a chemical sensor detection process implemented in accordance with the teachings of the present disclosure.

Key steps in a surveillance or chemical detection process 500 are summarized with the flowchart depicted in FIG. 5. Steps in the flowchart can be described as follows:

Disperse RIMs 505: RIMs are dispersed over a variable area of interest, or a set of articles. As one example, RIMs can be embedded on the surface of common objects or articles. Alternatively, they can be dispersed as an aerosol and applied as a thin chemical detection coating/layer.

Exposure 510: RIMs are exposed to an environment at the site or article that may include target chemical or biological agents.

Sense 515: A circuit (or circuits) is activated and detects the presence or absence of one or more targets. Activation of the circuit may occur once or on multiple occasions with predetermined timed intervals. Activation may occur in response to externally applied trigger signals.

Record Data 520: The circuit writes the result to nonvolatile memory in binary form.

Analyze Data 525: The data are compared with benchmark values stored in memory. The comparison determines if the result meets a threshold of significance.

Create a readout marker 530: If a target agent is identified, a structure or chemical is created or enabled as a marker that responds, at a later time and under appropriate circumstances, to externally applied electromagnetic or optical radiation.

The above steps detect a specific target agent that responds only to narrowly specific analytic techniques. The result is converted to a marker that is readily detected by common and readily available techniques involving, for example, optics or longer wavelength electromagnetic waves.

Recover RIMs 540: The RIMs can be optionally collected and recovered. For example, if RIMs are attached to a carrier article, that article can be recovered at an appropriate facility.

Alternatively, Move Readout Receiver to Field site of RIMs 535: The Receiver is moved to a location proximal with the distributed RIMS to detect their state.

Readout Results 545: The Readout Receiver may receive an active transmission from one or more RIMs (active mode). Alternatively, the Receiver may interrogate the RIMs with optic or electromagnetic radiation and receive (detect) a response (passive mode).

Output Results to Information Network 550: The Readout Receiver stores the results and makes them available to an information network.

Novel Application/Distribution Techniques

Another focus of this disclosure is the consideration of applications of the RIM based detector that involve surveillance or reconnaissance of an illegal activity involving dangerous and/or illicit chemical or biological agents. For example, an individual involved in an illegal and/or harmful activity may be working with these materials in a secluded and/or confined area to avoid detection. Any dangerous and/or illicit chemical or biological material associated with such activity can be a target of inspection. To detect such illegal activities, different mechanisms to surreptitiously introduce RIM detectors to the area/location can be used so that they are placed in sufficient proximity to the target of inspection. The RIMs are initially set to be dormant or inactive. When activated, the RIM detectors perform a logical detection test routine in order to sense whether a target detected substance is a dangerous or illicit chemical and then record a response that indicates whether the test is positive. The RIM detectors are then collected and queried. Alternatively, the RIM detectors may remain dispersed in their sensing location but queried remotely. In any case, it is preferable, of course, in such surveillance applications, that the RIM detectors and their readout markers should not be observed (or be observable) by the targeted individual(s).

Figure 6:
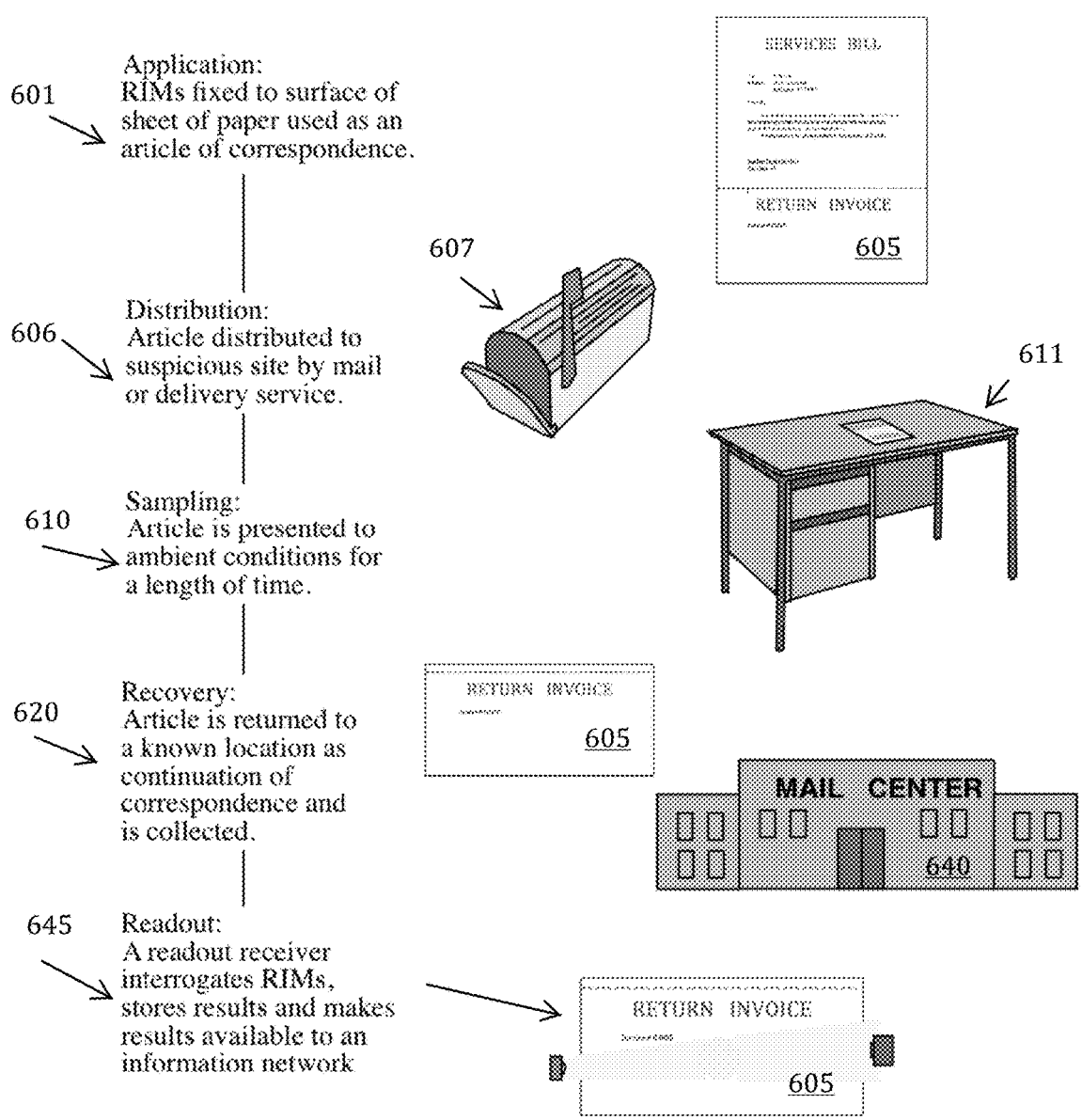
FIG. 6 is a simplified flowchart of the basic steps of a preferred chemical sensor detection process, using RIMs embedded in an article, implemented in accordance with the teachings of the present disclosure.

One embodiment of a detector application/distribution method 600 is depicted with the flow chart in FIG. 6. At step 601 any number of RIM detectors can be fixed to (or coated on) the surface of a sheet of paper, another paper based product (paper towel, envelope, box, air filter, paper mask, product packaging, book, passport, travel documents etc.), or any other convenient article 605 which has surface characteristics that allow for adherence of the RIM detectors. In a preferred paper article embodiment, the process of "fixing" is meant to imply that each RIM is pressed into the surface of the paper with sufficient pressure (or attached with a secondary adhesive so) that it adheres to the surface. In some instances they may be incorporated within the fibers of the paper directly as part of a paper making process. For example, passports may include exterior binding paper or internal sheets in which the elements are incorporated. In other instances a liquid adhesion mixture can be applied to form a thin layer of detection elements, and such that after exposure to air a carrier liquid evaporates, leaving the RIMs on the surface of the article. Because of their small size, however, the loss of some number of detectors from being peeled off or otherwise removed should not be detectable. The RIM preferably has a placement at or near the surface so that volatile molecules in the ambient environment (or on the hands of the targeted individual or some other surface) can come in contact with the sensor surface.

The paper then can be introduced into the target location inconspicuously as an article of correspondence, advertising, packing receipt, etc. at step 606 to a target location 607. The RIMs 300 will not be observable by a targeted individual with the naked eye because they are microscopic in size. After spending sufficient time at step 610 in the target location 611, the paper (or other article) can be recovered in the form of waste or of a continued correspondence, or any other suitable form at step 620. Once recovered, the RIMs 300 on the paper can be tested at a facility 640 to determine their status at step 645.

In a variation of this first embodiment, some forms of RIM detectors can be imprinted to a paper article 605 within a print ink/dye or toner mixture, as part of a printing process, or photocopying process. For example, in a conventional ink jet printer, the ink drops are approximately 100 microns in size. By engineering the RIM detectors 300 to be much smaller than this and have reasonable resistance to heat, it is expected that they can be accommodated and printed by a typical printing head by their incorporation within a larger inkjet droplet.

In dry toner applications, the RIM detector 300 can be included as part of the print powder mixture. The size of toner particles (which form the bulk of the mixture) is extremely small (typically on the order of 10 microns) and therefore the detectors (which form the detecting part of the mixture) must be of equivalent size, weight and preferably shaped in a similar manner to the toner particles to exhibit similar adhesion characteristics. In this manner the detectors are able to adhere to paper using the same or similar mechanism as the toner particles, i.e., using electrostatic, magnetic and/or surface tension attractions. It will be understood that the imparting of the detectors to the paper may be achieved by a separate dedicated pre or post print station within a printer apparatus as well.

In such applications it is expected that some portion of the RIM detectors may be rendered unusable if they are completely covered with ink/toner. However, as long as a reasonable number are exposed on a printed surface they can react with a target chemical to yield useful testing and results. Furthermore, in applications for detection of an environmental condition (such as temperature) the mixing or lack of surface exposure may be less critical, again, subject to the RIM detector state being readily detectable/readable. For ease of use and flexibility, in a printing application the inclusion of RIM detectors may be implemented on a selective character by character basis on a printed article. In this manner they can be selectively employed where necessary for an application In another embodiment of a distribution/application technique, a number of RIMs can be fixed to a piece of fabric, either directly or as part of a decal/logo. The process of "fixing" can be performed in the same manner as provided above. In some instances the RIM detectors can introduced to a surface portion of the body of the article during a washing/drying process depending on the fabric properties, size/adherence of the RIMs, etc. For example, they may be incorporated within a solid/liquid detergent, or dryer paper softener, or other available mechanism. The piece of fabric is then introduced into the target location as an article of clothing provided to inhabitants or worn by a visitor surreptitiously to a targeted location. The fabric can be recovered and the RIMs can be tested to determine their status.

In a variant of this technique, an electronic skin compatible and flexible patch can incorporate the RIMs to detect the presence of particular chemicals, toxins, etc., in the sweat or other body fluid of a living organism. For example, some useful biomedical applications may include detection and measurement of alcohol and/or glucose in a person's sweat through flexible patches, tattoos, etc.

In yet another embodiment of a distribution/application technique, the RIMs can be aerosolized, or applied directly as a particulate aerosol to form a thin coating or layer of detection elements. An aerosol is a suspension of solid or liquid particles in a gas such as air or nitrogen. Typically the aerosol is contained in a pressurized container with a nozzle for dispensing the contents. The RIMs may form a dry aerosol or they can be mixed with a liquid, forming a suspension, and the liquid can be converted into an aerosol that is sprayed on any convenient surface to form an ultra-thin layer of detection elements.

A flowchart that describes an example of a process 700 for the distribution, sampling and testing of RIMs using an aerosol is provided in FIG. 7. In this example, an aerosol of RIMS is sprayed on the inside surfaces of the trunk of a rental car at step 710. The car is made available to a party that is under surveillance for illegal activity at step 715. The monitored party may store a dangerous and illegal substance in the trunk for some time at step 720. At step 725 the rental car is returned and the RIMs on the inside surfaces of the trunk are queried at step 730 for example using an optical sensor. It will be understood that this example is presented with the article in question being a vehicle, and similar steps may be employed to distribute and sample other articles, including consumer products or other items that are handled by humans in every day activities.

To provide a further description of application and distribution using aerosol, the particulate portion of an aerosol is called the Particulate Matter or PM. PM is measured as a particle diameter and is denoted typically in units of microns. The PM in a conventional aerosol can usually range from 0.001 to 100 microns. Typical diameters of RIMs discussed in this invention application preferably range from 1 to 100 microns and therefore qualify as equivalent in size to Very Fine or smaller droplets (according to the ASABE S572.1 Droplet Size Classification Chart) and can form a particulate aerosol suspension. This size range is the same as atmospheric dust (diameters of 50 microns and smaller) and coal dust (diameters of 1 to 100 microns) and consequently RIM detectors in an aerosol can be expected to have characteristics of dispersion and adhesion that are similar to aerosols of atmospheric or coal dust.

In other instances the RIMs can be mixed with a liquid (e.g. water, methanol) so that a RIM coated with the liquid can form an aerosol suspension. In either case, the density of the aerosol can be controlled in any conventional manner. The RIM detector aerosol can be applied to a target surface of an article as a spray using the liquid as a carrier and the RIM detector particulates. Similar to dust, RIM detectors can be expected to stick to many surfaces by normal forces of adhesion. Furthermore, it is expected that adhesion to particular surfaces can be optimized using routine skill based on adjusting surface textures, particle size/weight, etc. For example the weight/shape/texture of a RIM detector can be altered as desired using routine skill during manufacturing form by including an additional backing/coating or surface treatment.

In some applications a number of controlled RIM aerosol treatments can be performed at a location (akin to how pest control services or pest "bombs" work) to prepare an area, site or enclosed building for testing. By blanketing and interrogating an entire enclosed space, opportunities are created for detecting other potential chemicals, leaks, etc. After the liquid carrier evaporates, the aerosol based RIMs will adhere to the surface so that the sensor can be presented to ambient conditions. It will be understood by those skilled in the art that it may not be necessary to use a pressurized container, and the RIM detectors may be applied in suspension, or part of another liquid, as long as they can be reasonably and uniformly applied and exposed after the carrier/suspension liquid evaporates. For example, some types of personal care products (perfume, lotion, solid/liquid soaps, shampoos, sprays, hand sanitizers) and even potable water may be modified to include a desired concentration and number of the novel RIM detectors. The RIM detectors would then adhere to a person's (or other organism) skin, hair, etc. so that they become active, mobile sensors tracking the person's exposure. Since the RIM detectors are biologically inert they also can be incorporated in small doses in food products for detection of some internal condition or target material.

The aerosolized RIM detector spray may be also applied to walls, ceilings, windows of structures, containers or personal articles such as tools and cars. For example, in a surveillance application, it may be desirable to coat window panes with a thin film that reacts to ambient within an area and is detectable from outside a structure. As before, the RIMs can be recovered by removing them from the surface with a cloth and an appropriate solvent.

In commercial applications the RIM detectors can be implemented as desired on different correspondence/articles to solicit information on the presence of particular chemicals in consumer's homes, rental vehicles, etc. For example, the presence of particular food odors, fragrances, pet smells, ambient household scents, or any other target chemical can be detected and acted on for marketing and sales purposes. The presence of chemical markers in a rental vehicle (cigarette smoke, drugs) may be used to identify violations of rental contract agreements, as in the case of consumers transporting unauthorized substances. In industrial applications, the exposure by workers to target chemicals can also be detected and analyzed to determine compliance with safety standards. For example, the RIM detectors can be incorporated within work clothing, masks, gloves, or other surface, and interrogated regularly during a workday to identify exposure to specific chemical elements, including any harmful or undesirable substances. The detection process may be done with or without the knowledge of employees to increase security, maintain privacy, etc. A similar process could be adopted within a secure facility, including a penitentiary, to detect interactions by inmates with improper or illegal substances.

Readout Receiving

As described in '021 and mentioned above, the result that is stored in the RIM sensor chip can be represented by the creation of a readout marker. A readout receiver (410 in FIG. 4) addresses, receives and interprets the marker to make that result available to an information system. In one implementation of this technique that was described above, two component chemicals are separated by a membrane and an output pulse to a MEMS or NEMS device ruptures the membrane enabling the two constituents to form a dye. Alternatively, a dye molecule can be stored inside a volume bounded by a membrane. An output pulse ruptures the membrane and allows the dye to escape, adhere to the surface of the RIM, and thereby become visible or detectable by an instrument/machine. There are many optical techniques that are highly sensitive for the detection of trace quantities of die. To detect small quantities of dye, for example on a page of paper or other article, one standard technique is described as follows. White light is directed at the article (e.g. paper) and the reflected light is recorded by two separate detectors. The detectors can by photo-diodes or photo multiplying cells. To detect red dye, for example, one detector is sensitive to red light and the second is sensitive to green light. The output of the two detectors is compared. A recorded output from the red photo-detector that is larger than that from the green photo-detector can be determined with high sensitivity.

Alternatively, one can substitute a fluorescent molecule for the dye molecule. In this case, detection involves applying a pulse of ultra violet light to the article. The ultra violet creates excitations in the fluorescent molecules and the excitations decay by emitting photons of visible light. Detection involves timing the shutter of a photo-detector to open immediately after the termination of the ultra violet pulse.

As is apparent from the above discussion, the particular sensor form and detection mechanism can be tailored, customized and optimized based on a target application. Furthermore, in analogy with "Field Programmable Gate Array" technology, multiple sensors and associated circuitry can be fabricated on any RIM. The user can programmatically choose the sensors to be used. Circuits and/or chip sectors associated with individual sensors can be activated or inactivated by using fuses or antifuses, or nonvolatile switches as disclosed in U.S. Pat. No. 9,735,344. An advantage of this approach is that manufacturing a single RIM design can address a variety of different sensing needs. This provides more flexibility for applications. The results of a number of sensors can be stored in nonvolatile memory and read out by techniques described in earlier text.

Sensors of Environmental Conditions

Previous discussion has described one focus of this disclosure, applications of the RIM based detector that involve surveillance or reconnaissance of an illegal activity involving dangerous and/or illicit chemical or biological agents. Other applications that use the same methods are apparent. The inventive RIMs can be used for detecting environmental conditions as well, such as temperature, humidity, light, radiation, etc. FIG. 3 can be used to depict a RIM with a temperature sensor as structure 330, rather than a chemical adsorbent. The RIM may be programmed to activate the sensor periodically. Alternatively, the RIM may be periodically activated by a microwave pulse. In either case, if the temperature exceeds a threshold value, an output would trigger an event that would be detected externally. The events and detection could be implemented in the same manner as described for the RIM with a chemical sensor.

Currently there are two kinds of temperature sensors that are commonly used with integrated circuits. Either or both can be made with a microfabrication process and could be used in connection with embodiments of the present invention for detecting environmental conditions.

(1) Resistance Temperature Detector (RTD).

RTDs commonly use a thin metal film resistor. Platinum (Pt) resistors can be used over a large temperature range, −200 to 600 C. Of course, most chips that include semiconducting devices operate in a reduced range of 0 to 100 C and will not be suitable for performance in a broader temperature range. As an example of plausibility, an appropriate metal film resistor can be designed with the following considerations. Thin film Pt has resistance per square of about 1 Ohm for a thickness of about 30 nm. A thin film wire could be fabricated with 400 nm (0.4 um) width. A ten micron length then has resistance of 25 squares=25 Ohms. The wire could be formed as a meander line with 4 repeats that giving a total resistance of 100 Ohms. A bias current of 100 microAmps produces a voltage of 10 mV which is readily detected with good accuracy. Careful analysis will determine the requirements for a given application. For example, if threshold at 100 C is desired an integrated sense amplifier that has an appropriate accuracy can be engineered using known techniques. Similarly, the output voltage would be adjusted so that the sense amplifier has the required accuracy.

(2) Semiconductor-Based Sensors:

These sensors typically are comprised of two identical diodes that have voltage-current (V-I) characteristics that are sensitive to temperature and therefore can be used to monitor temperature changes. They offer a linear response but have lower accuracy (about 1 to 5 C) than RTDs. As noted above, they also have a narrower temperature range (−70 to 150° C.).

For applications related to environmental conditions, the size of the RIM may not be crucially important. It may therefore be convenient to manufacture the RIM with dimensions of order 1 to 10 millimeter. In this case, microwave readout techniques can employ dipole antennas with relatively large dimensions. Passive dipole antennas can be detected at relatively large distances. The larger RIM may include a larger battery with circuitry to increase the detection distance. A larger RIM, as described in this paragraph, has several advantages in comparison with prior art RFID tags. Conventional RFID tags may contain the order of 100 bits of information, but these data are of the form "write once, read many." The data may be an identification code or serial number, for example. But that number was written to nonvolatile memory and cannot be changed. By contrast, the RIM is a dynamic device that can perform sense and analysis operations. The RIM may contain information bits that provide identification. Of greater importance, the RIM can perform operations and add (or change) data that are stored in memory during the lifetime of operation. These data may represent, for example, a history of temperature or of exposure to other environmental conditions such as humidity or a variety of forms of radiation.

The examples above are merely illustrative of the general principles inherent in the teaching of the present invention. Other variations will be apparent to skilled artisans, and the present invention should not be interpreted to be restricted to such specific embodiments and examples.

What is claimed is:

1. A method of detecting target chemicals comprising the steps of:
   providing a first physical article;
   embedding a chemical detection element onto a surface portion of said physical article, wherein each of the chemical detection elements comprises a single integrated circuit (IC);
   generating a sensor state based on a sensor element on said single IC, which sensor state responds to the presence of a target chemical on and/or near said first physical article;
   generating a transducer output with a transducer on said single IC coupled to the sensor element which detects said sensor state and generates an output corresponding thereto;
   interpreting said transducer output with a magnetoelectronic (ME) processing element on said single IC;
   wherein said ME processing element generates a detection value based on said interpreting said output confirming the presence of said target chemical;
   generating a chemical payload output responsive to said detection output on the single IC to indicate exposure of said first physical article to said target chemical.

2. The method of claim 1 wherein said chemical payload includes a readout substance situated in a storage chamber of said single semiconductor chip and one or more micromechanical structures responsive to said detection output, cause said first readout substance to be released from said chamber in response to said detection value.

3. The method of claim 1, further including a step: applying said chemical detection element as a liquid to said physical article.

4. The method of claim 1, further including a step: applying said chemical detection element as a spray to said physical article.

5. The method of claim 4 wherein said spray is in aerosol form.

6. The method of claim 1, further including a step: applying said chemical detection element in solid form to said physical article.

7. The method of claim 1 further including steps: placing said physical article in a target environment; and recovering said physical article after a predetermined period.

8. The method claim 1 further including steps: moving a readout receiver to a target environment where the physical article is located and reading said chemical payload output.

9. The method of claim 1 wherein said physical article is a piece of paper.

10. The method of claim 1 wherein said physical article is an article of clothing.

11. The method of claim 1 wherein said physical article is part of an enclosure for a room.

12. The method of claim 1 wherein said physical article is a transportation vehicle.

13. The method of claim 1 wherein said physical article is a fixture or piece of furniture within a room.

14. A method of detecting hazardous materials comprising the steps of:
provic a first physical article;
embedding a chemical detection element onto a surface portion of said physical article, wherein each of the chemical detection elements comprises a single integrated circuit (IC);
generating a sensor state based on a sensor element on said single IC, which sensor state responds to the presence of a target hazardous chemical on and/or near said first physical article;
generating a transducer output with a transducer on said single IC coupled to the sensor element which detects said sensor state and generates an output corresponding thereto;
interpreting said transducer output with a magnetoelectronic (ME) processing element on said single IC;
wherein said ME processing element generates a detection value based on said interpreting said output confirming the presence of said target hazardous chemical;
a microwave antenna coupled to the ME processing element and responsive to an interrogation signal to enable passive readout of said detection value;
wherein a presence of said target hazardous chemical can be determined by interrogating said stored detection value.

15. A method of detecting targeted chemical materials comprising the steps of:
providing a first physical paper article;
embedding a chemical detection element onto a surface portion of said first physical paper article, wherein each of the chemical detection elements comprises a single integrated circuit (IC);
configuring said first physical paper article into correspondence to a first target individual;
delivering said first physical paper article to a target location for said target individual by public mail or private delivery service;
sampling a target environment at said target address to detect the presence of a target chemical;
generating a sensor state based on a sensor element on said single IC, which sensor state responds to the presence of said target chemical on and/or near said first physical paper article;
generating a transducer output with a transducer on said single IC coupled to the sensor element which detects said sensor state and generates an output corresponding thereto;
interpreting said transducer output with a magnetoelectronic (ME) processing element on said single IC;
wherein said ME processing element generates a detection value based on said interpreting said output confirming the presence of said target chemical;
generating a chemical payload output responsive to said detection output on the single IC to indicate exposure of said first physical paper article to said target chemical;
receiving said first physical paper article in the form of return correspondence at a separate facility;
reading said chemical payload output to determine exposure of said chemical detection element to said first target chemical.

* * * * *